United States Patent [19]

Tóth et al.

[11] Patent Number: 4,764,613
[45] Date of Patent: Aug. 16, 1988

[54] 2,6-BIS(CHLOROMETHYLOXY-CARBONYLOXYMETHYL)PYRIDINE AND A PROCESS FOR PREPARING SAME

[75] Inventors: József Tóth, Budapest; Máté Kovatsits, Leányfalu; László Csutorás, Budapest; Gábor Szabo, Budapest; Sándor Görög, Budapest; Ferenc Trischler, Budapest; Sándor Holly, Budapest; Erzsébet Francsics, Budapest; Béla Losonczi, Budapest; Gábor Havasi, Dorog, all of Hungary

[73] Assignee: Richter Gedeon Vegyeszeti Gyar Rt., Budapest, Hungary

[21] Appl. No.: 88,875

[22] Filed: Aug. 24, 1987

[30] Foreign Application Priority Data

Aug. 22, 1986 [HU] Hungary ............................. 3654/86

[51] Int. Cl.$^4$ ........................................... C07D 213/55
[52] U.S. Cl. ................................................... 546/341
[58] Field of Search ........................................ 546/341

[56] References Cited

PUBLICATIONS

Morrison et al., Org. Chem., 3rd Ed., pp. 456–457 (1978).

Primary Examiner—Mary C. Lee
Assistant Examiner—J. Richter
Attorney, Agent, or Firm—Herbert Dubno; Jonathan Myers

[57] ABSTRACT

The invention relates to the novel 2,6-bis(chloromethyloxy-carbonyloxymethyl)pyridine of the formula (I)

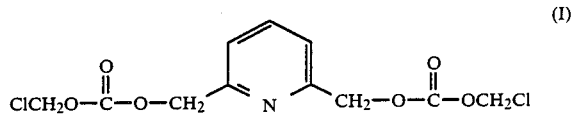

as well as a process for the preparation of this compound, which is a useful intermediate in the preparation of the anti-atherosclerotic 2,6-bis)hydroxymethyl)pyridine bis(N-methylcarbamate) (pyridinolcarbamate) and other drugs.

According to the invention, the compound of the formula (I) is prepared by reacting 2,6-bis(hydroxymethyl)pyridine of the formula (II)

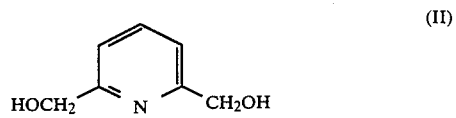

with chloromethyl chloroformate of the formula (III)

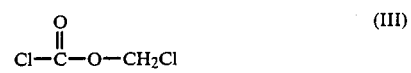

in a polar-aprotic, water-immiscible organic solvent, in the presence of a basic substance between about −30° C. and +10° C.

1 Claim, No Drawings

2,6-BIS(CHLOROMETHYLOXY-CARBONYLOXYMETHYL)PYRIDINE AND A PROCESS FOR PREPARING SAME

The invention relates to the novel compound 2,6-bis(chloromethyloxy-carbonyloxymethyl)pyridine of the formula (I)

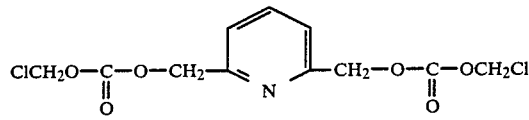 (I)

as well as to a process for the preparation of this compound.

The compound of the formula (I) is an important intermediate for the preparation of 2,6-bis(hydroxymethyl)pyridine bis(N-methylcarbamate) (generic name: pyridinolcarbamate). Pyridinolcarbamate which is a known drug with a useful anti-atherosclerotic and anti-inflammatory action, can be prepared from the novel compound of the formula (I) as described in Example 2.

The novel compound of the formula (I) is also a useful intermediate for the preparation of other drugs, particularly of carbamate esters.

Concerning the novel compound of the formula (I), no reference was found in the literature.

According to an other aspect of the invention, there is provided a process for the preparation of the novel compound of the formula (I), which comprises reacting 2,6-bis(hydroxymethyl)pyridine of the formula (II)

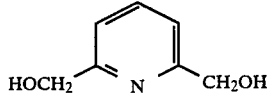 (II)

with chloromethyl chloroformate of the formula (III) in a polar-aprotic, water-immiscible organic solvent, in the presence of a basic substance at a temperature below 10° C.

2,6-bis(hydroxymethyl)pyridine of the formula (II) may be prepared according to the literature, as described e.g. in the Japanese patent specification No. 68-14,222. Chloromethyl chloroformate of the formula (III) may be prepared as described e.g. in the published German patent application No. 3,241,568.

As the water-immiscible solvent, e.g. acetonitrile; dimethylformamide; dioxane; tetrahydrofuran; ethyl acetate; ethers; aromatic hydrocarbons such as benzene, toluene; and preferably halogenated hydrocarbons such as chloroform or dichloromethane may be used.

As a basic agent, e.g. organic bases such as triethylamine; trimethylamine; N-methylmorpholine; pyridine, preferably pyridine, may be used.

The reaction of the compound of the formula (II) with the compound of the formula (III) is carried out at a temperature between −30° C. and +10° C., preferably at about −5° C. This reaction will be described in detail hereinafter. At least 2 moles of chloromethyl chloroformate of the formula (III) [as calculated for 2,6-bis(hydroxymethyl)pyridine of the formula (II)] are dissolved in the desired solvent, preferably in chloroform, and a solution containing an organic base, preferably pyridine, in the same molar amount as the compound of the formula (III) in the same solvent is added at a temperature lower than 10° C., preferably at about −5° C., under stirring. The suspension obtained is stirred for about 20 minutes while care is taken to avoid any increase of the temperature. Then, 2,6-bis(hydroxymethyl)pyridine of the formula (II) is added to the above mixture at the same temperature at such a rate that the temperature reaches at most −5° C. The suspension is stirred for about 20 minutes to give a brown solution. After washing this solution with water and evaporation, a practically pure product with 95 to 97% of 2,6-bis(chloromethyloxy-carbonyloxymethyl)pyridine content is obtained. The product obtained after washing with water and making free of the solvent can be used without any purification or, if desired, may be further purified by chromatography on a silicagel column or on an other adsorbent, e.g. on a synthetic resin.

The physical constants of the thus-obtained product were determined by using gas chromatography on a 3% OV-210 column at 210° C.

The process of the invention is illustrated in detail by the following non-limiting Examples.

EXAMPLE 1

Preparation of 2,6-bis(chloromethyloxy-carbonyloxymethyl)pyridine

To a solution containing 13.0 g (0.1 mole) of chloromethyl chloroformate in 40 ml of chloroform, 8 ml (0.1 mole) of pyridine dissolved in 40 ml of chloroform are added at −5° C. at such a rate that the temperature is maintained at −5° C. or lower. A suspension is formmed which becomes more and more thick. After completion of the addition, the reaction mixture is stirred at about −5° C. for 15 minutes, then 5.6 g (0.04 mole) of 2,6-bis(hydroxymethyl)pyridine are added to the mixture at the same temperature in several portions at such a rate that the temperature does not increase. During the addition, the mixture becomes thinner and after a stirring for about 20 minutes, a solution of brown color is obtained. After completion of the stirring, 120 ml of water are added to the mixture under vigorous stirring. The aqueous phase is separated from the organic one and extracted twice with 40 ml of chloroform each. The chloroformic phases are combined, washed with 20 ml of water and dried over anhydrous magnesium sulfate. After filtration, the solvent is evaporated and the residue is made free from any solvent under vacuum. Thus, 12.2 g of a honey-like oil with a characteristic mildly sharp odor are obtained which contains more than 96% of 2,6-bis(chloromethyloxy-carbonyloxymethyl)pyridine according to the chromatographic measurements. The yield is 98% as calculated for 2,6-bis(hydroxymethyl)pyridine.

Analysis: Cl calculated: 21.39%. Cl found: 21.19%.

IR (cm$^{-1}$): C=O 1765; C—O—C 1250; C—Cl 723; aromatic skeleton 1600, 1582; Ar—H def. 790.

$^1$H-NMR (CDCl$_3$δ, ppm): 5.3 (s, Ar—CH$_2$—O); 5.74 (s, Cl—CH$_2$—O); 7.2–7.9 (m, Ar—H).

EXAMPLE 2

Preparation of 2,6-bis(hydroxymethyl)pyridine bis(N-methylcarbamate)

3.15 ml of methanolic methylamine solution (containing 33.6% by weight, i.e. 0.024 moles, of methylamine) are added to a solution of 1.3 g (0.004 moles) of 2,6-bis(chloromethyloxy-carbonyloxymethyl)pyridine (prepared as described in Example 1) at about 0° C. under cooling at such a rate that the temperature is maintained at 10° C. or lower. A crystalline precipitate is separated. After completing the addition, 5 ml of water are added to the mixture which is then cooled to 2° to 5° C. The precipitate is separated by filtration and dried to give 0.97 g of the title compound, m.p.: 132°–135° C. The yield is 97% as calculated for 2,6-bis(hydroxymethyl)-pyridine. The 2,6-bis(hydroxymethyl)pyridine bis(N-methylcarbamate) content of the thus-obtained product is 98% based on the spectrophotometric determination.

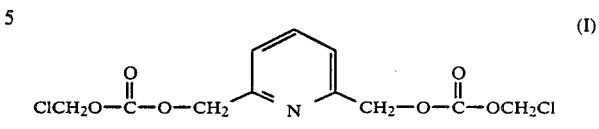

We claim:
1. 2,6-bis(chloromethyloxy-carbonyloxy-methyl)-pyridine of the formula (I)